United States Patent [19]

Ernst et al.

[11] Patent Number: 4,716,243

[45] Date of Patent: Dec. 29, 1987

[54] α-(O-CHLOROPHENYL)-AMINOMETHY-LENE-β-FORMYLAMINOPROPIONITRILE

[75] Inventors: Hansgeorg Ernst, Ludwigshafen; Wolfgang Littmann, Mannheim; Joachim Paust, Neuhofen, all of Fed. Rep. of Germany

[73] Assignee: BASF Aktiengesellschaft, Ludwigshafen, Fed. Rep. of Germany

[21] Appl. No.: 765,505

[22] Filed: Aug. 15, 1985

[30] Foreign Application Priority Data

Aug. 25, 1984 [DE] Fed. Rep. of Germany ....... 3431270

[51] Int. Cl.⁴ .................. C07C 87/24; C07C 121/16; C07D 239/42
[52] U.S. Cl. ................................ 558/395; 544/329
[58] Field of Search .................... 558/395; 544/329

[56] References Cited

U.S. PATENT DOCUMENTS 3,954,756  5/1976  Maruyama et al. ............... 558/395
4,226,799 10/1980  Brewert et al. .................. 558/395

FOREIGN PATENT DOCUMENTS 0001760 10/1978 European Pat. Off. ............ 558/315
2323845 11/1973 Fed. Rep. of Germany ...... 558/395

*Primary Examiner*—Henry R. Jiles
*Assistant Examiner*—J. G. Mullins
*Attorney, Agent, or Firm*—Keil & Weinkauf

[57] ABSTRACT

α-(o-Chlorophenyl)-aminomethylene-β-formylaminopropionitrile, process for its preparation by reacting a metal salt of α-formyl-β-formylaminopropionitrile with a salt of o-chloroaniline in an aqueous medium, and use of the product to prepare the compound of the formula

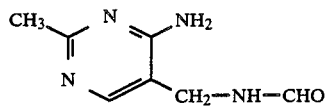

by reaction with acetamidine. The pyrimidine thus obtained is an intermediate for the preparation of vitamin $B_1$.

1 Claim, No Drawings

α-(O-CHLOROPHENYL)-AMINOMETHYLENE-β-FORMYLAMINOPROPIONITRILE

The present invention relates to a particular N-substituted α-aminomethylene-β-formylaminopropionitrile which is used for the preparation of 2-methyl-4-amino-5-formylaminomethyl pyrimidine II, and its preparation from a metal salt of α-formyl-β-formylaminopropionitrile III. Compound II is an important intermediate in the preparation of vitamin $B_1$.

European Pat. No. 0,001,760 discloses an advantageous process for the preparation of 2-methyl-4-amino-5-formylaminomethylpyrimidine II

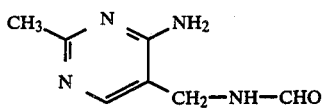

wherein a salt of α-formyl-β-formylaminopropionitrile III

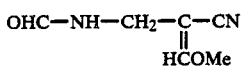

where Me is a cation, preferably an alkali metal cation or alkaline earth metal cation, is reacted with a salt of ammonia or of an amine of the formula

where the radicals R are hydrogen or identical or different alkyl, aryl or aralkyl radicals or together with the nitrogen atom form a heterocyclic ring, to give a novel α-aminomethylene-β-formylaminopropionitrile of the formula I

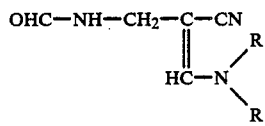

where R has the above meaning, the latter compound then being cyclized with acetamidine to give the pyrimidine II.

The said European patent mentions N-methylaniline and aniline as aromatic amine components, and in particular describes the anilino compound as a starting material for further conversion to the pyrimidine of the formula II.

We have now found, surprisingly, that particularly high yields and, at the same time, a shorter time of reaction with the pyrimidine of the formula II

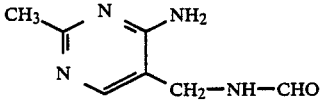

are achieved if α-(o-chlorophenyl)-aminomethylene-β-formylaminopropionitrile of the formula I'

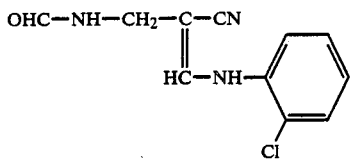

is cyclized with acetamidine.

The compound of the formula I' is obtained in a manner known per se from EP-B No. 0,001,760 when a salt of α-formyl-β-formylaminopropionitrile III

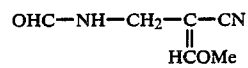

where Me is a cation, preferably an alkali metal or alkaline earth metal cation, is reacted with a salt of ortho-chloroaniline.

The preparation of the starting materials of the formula III is described in EP-B No. 0,001,760, which is herewith incorporated by reference.

Examples of suitable salts of o-chloroaniline are the sulfate and the salts of the hydrohalic acids, especially the hydrochloride.

The reaction of a salt of o-chloroaniline with a salt of α-formyl-β-formylaminopropionitrile is advantageously carried out in an aqueous medium, starting with a suspension of the o-chloroaniline salt and, for example, adding the sodium salt of α-formyl-β-formylaminopropionitrile at normal or slightly elevated temperature, for example at up to 40° C. This directly gives the desired compound of the formula I' in crystalline form.

The further reaction of the novel compound of the formula I' with acetamidine, to give the pyrimidine II, is carried out in the manner described in German Laid-Open Application DOS No. 2,323,845 for the starting material α-alkoxymethylene-β-formylaminopropionitrile. The reaction can be carried out in the presence of an inert solvent. Suitable solvents are those mentioned in the said DOS No. 2,323,845 as well as other inert solvents, for example acetonitrile and dimethylformamide, and also the o-chloroaniline liberated during the reaction.

When using the novel α-(o-chlorophenyl)-aminomethylene-β-formylaminopropionitrile, the yield obtained is about 8% higher than when using the corresponding p-chloroanilino compound and even about 15–20% higher than when using the corresponding anilino compound; the reaction time is shortened from 18–20 hours to 30–60 minutes, and less excess of acetamidine is required.

EXAMPLE 1

(a) 200 ml of concentrated hydrochloric acid are added to a mixture of 382.5 g (3 moles) of o-chloroaniline and 600 ml of water, while cooling with water. A solution of 444 g of the sodium salt of α-formyl-β-formylaminopropionitrile (90.65% Δ2.72 moles) in 1,500 ml of water is then added dropwise over about 30 minutes at 25°–30° C., with stirring. At the same time, the pH is kept at 1.3 by adding concentrated hydrochloric acid.

Stirring is continued overnight at room temperature, the product is filtered off and washed twice with about 1 liter of water at a time and the filter cake is dried overnight at +50° C. in a vacuum oven.

Weight of product: 625.2 g (97.6% of theory) of α-(o-chlorophenyl)-aminomethylene-β-formylaminopropionitrile.

The product is pure according to NMR spectroscopy.

(b) 23.6 g (0.10 mole) of the enamine obtained as above are introduced into 20 ml of acetonitrile. 13.4 g of acetamidine (86.4% pure 0.20 mole) are added dropwise over 20 minutes at 50° C. The temperature slowly rises to 61° C. and then drops again, over about 30 minutes, to +50° C. Stirring is continued for about 15 minutes at +50° C., so that the total reaction time is 60 minutes. The reaction mixture is allowed to come to room temperature, 20 ml of diethyl ketone are added, the batch is stirred briefly and filtered, the filter cake is washed twice with 50 ml of diethyl ketone at a time, and the product is dried in a stream of $N_2$.

Weight of product: 14.27 g (86.0% of theory) of formylaminomethyl-aminopyrimidine.

Melting point: 219°–220° C.
Purity: 95.9%.

(c) To 23.6 g (0.10 mole) of enamine according to paragraph (a), in 20 ml of acetonitrile, are added dropwise 13.4 g of acetamidine (containing 13.6% by weight of MeOH; 0.20 mole) over 20 minutes at 50° C.

The mixture is then stirred for 5 minutes at 50° C., during which the internal temperature rises to +62° C. Acetonitrile is stripped off under reduced pressure from a water pump, and the reaction mixture is stirred under reduced pressure for another 45 minutes, while being kept at +50° C. The total reaction time after completion of addition of the acetamidine is 1 hour. 80 ml of isopropanol are then added, the mixture is heated under reflux for 10 minutes, cooled to +5° C., stirred for 15 minutes at that temperature and then filtered; the filter cake is washed twice with 50 ml of isopropanol at a time and is dried in a stream of $N_2$.

Weight of product: 13.85 g (83.4% of theory) of formylaminomethyl-aminopyrimidine.

Melting point: 219°–221° C.
Purity: 98.8%.

EXAMPLE 2

(a) 9 ml of concentrated sulfuric acid are added to a mixture of 31.9 g (0.25 mole) of o-chloroaniline and 50 ml of water. A solution of 41.1 g of the Na salt described in Example 1 (90.65% pure; 0.25 mole) is then added dropwise over one hour, with stirring. Stirring is continued for 23 hours at room temperature and the product is filtered off, washed four times with 100 ml of water at a time and dried in a vacuum oven at +40° C.

Weight of product: 54.5 g (92.6% of theory) of α-(o-chlorophenyl)-aminomethyl-β-formylaminopropionitrile.

Melting point: 124°–126° C.

(b) 23.6 g (0.1 mole) of the enamine obtained according to (a) are mixed with 13.05 g of acetamidine (88.9% pure; 0.20 mole) and the mixture is heated to 50° C. When the mixture has reached about 50° C., the exothermic reaction commences and the temperature rises within a few minutes to about 90° C. After a total reaction time of about 25 minutes, 100 ml of diethyl ketone are added, the mixture is stirred for 15 minutes at +50° C. and is allowed to cool to room temperature, the product is filtered off and the filter cake is washed twice with 50 ml of diethyl ketone at a time. The product is dried in a stream of $N_2$.

Weight of the product: 14.53 g (87.5% of theory) of formylaminomethyl-aminopyrimidine.

EXAMPLE 3

14 ml of concentrated hydrochloric acid are added to a mixture of 25.47 g (0.20 mole) of o-chloroaniline and 40 ml of water. To this suspension, a solution of 2.85 g of the Na salt described in Example 1 (90.3% pure=0.20 mole) in 100 ml of water is added dropwise over 15 minutes, with stirring. The pH is kept at 1.5 by simultaneously adding concentrated hydrochloric acid. Stirring is continued overnight at room temperature and the product is filtered off, washed three times with 100 ml of water at a time and dried in a vacuum oven at +40° C.

Weight of the product: 43.8 g=93.0% of theory of α-(o-chlorophenyl)-aminomethyl-β-formylaminopropionitrile.

EXAMPLE 4

(a) A mixture of 63.79 g (0.50 mole) of o-chloroaniline and 100 ml of water is brought to pH 1.2 with concentrated hydrochloric acid. Into this suspension is run a solution of 74.0 g of the Na salt described in Example 1 (90.3% strength=0.452 mole) in 250 ml of water, with stirring, over 20 minutes (during which the temperature rises to 37° C.) During the addition, the pH is kept at 1.2 by simultaneously adding concentrated hydrochloric acid.

Stirring is continued overnight at room temperature, the product is filtered off and washed three times with 150 ml of water at a time, and the filter cake is dried in a vacuum oven at 40° C.

Weight of the product: 99.5 g (93.5% of theory) of α-(o-chlorophenyl)-aminomethylene-β-formylaminopropionitrile.

(b) 27.61 g of acetamidine (84% pure, corresponding to 0.40 mole) are heated to 50° C. 47.1 g (0.20 mole) of the enamine from paragraph (a) are added, a little at a time, over 3 minutes. When the components have been mixed, an exothermic heaction commences (with the temperature rising to 110° C.); the reaction is allowed to finish, and the mixture is then stirred for 22 hours at 50° C. Thereafter 150 ml of diethyl ketone are added and the mixture is stirred for 30 minutes at 50° C. It is allowed to cool to room temperature and the product is filtered off and washed twice with 80 ml of diethyl ketone at a time. The filter cake is dried in a stream of $N_2$.

Weight of the prodcct: 31.71 g (95.5% of theory) of formylaminomethyl-aminopyrimidine.

Purity: 89%.

(c) In a further batch, 11.77 g (0.050 mol) of the o-chloroenamine according to paragraph (a) are added a little at a time, over 2 minutes, to 6.42 g of acetamidine (84% pure≧0.093 mole) at +50° C. After 5 minutes, the temperature of the reaction mixture rises to 88° C. in about 3 minutes, and then drops again to +50° C. In total, the mixture is left at a bath temperature of 50° C. for 1 hour; 40 ml of diethyl ketone are then added and stirring is continued for 30 minutes at +50° C. The product is filtered off and washed twice with 50 ml of diethyl ketone at a time, and the filter cake is dried in a stream of $N_2$.

Weight of the product: 7.85 g (94.6% of theory) of formylaminomethyl-aminopyrimidine.

Purity: 90.2%.

(d) To 3.53 g of acetamidine (84% pure, 0.051 mole), 11.77 g (0.050 mole) of the enamine according to paragraph (a) are added a little at a time, at 50° C., followed by 1 ml of dioxane. The mixture is then stirred for 4 hours at 50° C., 40 ml of diethyl ketone are added, and the mixture is stirred for a further 30 minutes at 50° C.

The product is then filtered off, washed twice with 50 ml of diethyl ketone at a time and dried. Weight of the product: 6.90 g (83.1% of theory) of formylaminomethyl-aminopyrimidine.

COMPARATIVE EXAMPLE 5

(a) 23.44 g (0.252 mole) of aniline are mixed with 25 ml of 36% strength hydrochloric acid. The suspension is dissolved by adding 20 ml of water. A solution of 41.66 g of the sodium salt described in Example 1 (88.8% pure; 0.250 mole) is added dropwise over 30 minutes, while keeping the pH at 2.0–2.5 by means of concentrated hydrochloric acid. The mixture is then stirred for 23 hours at room temperature and filtered. The filter cake is washed four times with 100 ml of water at a time and is dried in a vacuum oven at +45° C.

Weight of the product: 46.4 g (92.3% of theory) of α-phenyl-aminomethylene-β-formylaminopropionitrile.

(b) Yield of 2-methyl-4-amino-5-formylaminomethyl-pyrimidine obtained from α-phenylaminomethylene-β-formylaminopropionitrile and its time dependence:

20.0 g (0.1 mole) of the enamine from the preceding paragraph are added to 13.05 g of acetamidine (88.9% pure; ≧0.20 mole) at 50° C. Stirring is continued at 50° C., 80 ml of isopropanol are then added, the mixture is heated for 10 minutes under reflux, cooled to 5° C. and stirred at 5° C. for 15 minutes, and the product is filtered off. The filter cake is washed twice with 50 ml of isopropanol at a time and is dried in a stream of $N_2$.

| Duration of continuation of stirring at 50° C., h | Weight g | Formylaminomethyl-aminopyrimidine | | |
|---|---|---|---|---|
| | | Yield % | Melting point [°C.] | Purity |
| 5 | 9.44 | 56.9% | 221–221.5 | 96.3% |
| 7 | 10.04 | 60.5% | 220–221 | |
| 16 | 11.10 | 66.9% | 220.5–221 | |
| 18 | 11.32 | 68.2% | 221–221.5 | 96.6% |
| 24 | 11.22 | 67.6% | 221–221.5 | 96.0% |
| 48 | 11.32 | 68.2% | 221.5–222 | 97.0% |

If the acetamidine excess is reduced to 50 mole %, the yield of the pyrimidine derivative drops by 15–20%. If 1 equivalent of acetamidine is employed, the yield is halved.

We claim:

1. α-(o-Chlorophenyl)-aminomethylene-β-formylaminopropionitrile.

* * * * *